United States Patent [19]
Rapkin et al.

[11] 4,301,115
[45] Nov. 17, 1981

[54] TEST DEVICE RESISTANT TO CROSS CONTAMINATION BETWEEN REACTANT AREAS AND PROCESS FOR MAKING IT

[75] Inventors: Myron C. Rapkin; David L. Tabb, both of Elkhart, Ind.

[73] Assignee: Miles Laboratories, Inc., Elkhart, Ind.

[21] Appl. No.: 51,224

[22] Filed: Jun. 22, 1979

[51] Int. Cl.³ .................... G01N 21/00; G01N 31/22
[52] U.S. Cl. ........................................ 422/56; 422/57; 427/2; 435/805
[58] Field of Search .................... 422/55, 56, 57; 435/805; 427/2; 428/206

[56] References Cited

U.S. PATENT DOCUMENTS

| | | | |
|---|---|---|---|
| 3,127,281 | 3/1964 | Meyer | 422/57 X |
| 3,359,180 | 12/1967 | Evans et al. | 422/56 X |
| 3,552,929 | 1/1971 | Fields et al. | 422/56 |
| 3,592,679 | 7/1971 | Tulley et al. | 428/206 |
| 3,993,451 | 11/1976 | Verbeck | 422/57 |
| 4,160,008 | 7/1979 | Fenocketti et al. | 422/56 |
| 4,168,146 | 9/1979 | Grubb et al. | 422/8 X |

FOREIGN PATENT DOCUMENTS

| | | | |
|---|---|---|---|
| 6815866 | 5/1970 | Netherlands | 422/56 |
| 1240884 | 7/1971 | United Kingdom | 252/408 |

OTHER PUBLICATIONS

Boehbringer, Translation of Register Design German 1,852,316, May 24, 1962.

*Primary Examiner*—Arnold Turk
*Attorney, Agent, or Firm*—Edward H. Gorman, Jr.

[57] ABSTRACT

A test device for detecting the presence of constituents in a liquid test sample, and method for preparing it are disclosed. The device comprises a base support member coated with a hydrophobic barrier layer onto which is affixed a plurality of spaced apart reagents respectively responsive to different constituents of the test sample. The barrier layer comprises finely divided silica particles, to the surface of which are randomly covalently bound groups having the structure —O—SiR₃ wherein the R substituents, same or different, are hydrogen, lower alkyl or aryl.

13 Claims, 9 Drawing Figures

COMPARATIVE RESPONSES
TO OCCULT BLOOD IN URINE (COATED)

(UNCOATED)

TEST DEVICE RESISTANT TO CROSS CONTAMINATION BETWEEN REACTANT AREAS AND PROCESS FOR MAKING IT

BACKGROUND OF THE INVENTION

1. Field of the Invention

The present invention relates to a test device for detecting the presence of a constituent in a liquid test sample and method for making it. Moreover, it relates to minimizing the adverse effects of misuse of the device, thereby enhancing its accuracy and dependability.

The art of analytical chemistry has been greatly advanced since biochemistry began emerging as a primary scientific frontier, requiring increasingly sophisticated analytical methods and tools to solve problems, the solutions to which were never before attempted. Likewise, the medical profession has lent impetus to the growth of analytical chemistry, with its desiderata of both high precision and speed in obtaining results. This remarkable progress has been still further spurred by industries such as brewing, chemical manufacturing, and others.

To satisfy the needs of these expanding technologies, a myriad of analytical procedures, compositions and apparatuses have evolved, including solution chemistry techniques, automated machinery and the so-called "dip-and-read" type reagent strips. It is to the last of these that the present invention is primarily directed, although substantial benefit ultimately attaches to the other procedures as well.

Reagent strip test devices enjoy wide use in many analytical applications, especially in the chemical analysis of biological fluids, because of their relatively low cost, ease of utilizability and speed in obtaining results. In medicine, for example, numerous physiological functions can be monitored merely by dipping reagent strips into a sample of body fluid, such as urine, and observing a detectable response such as a change in color or a change in the amount of light reflected from or absorbed by the strip.

Compatible with such "dip-and-read" reagent strips have arisen many chemistries for detecting body fluid components. Many of these produce a detectable response which is quantitative or at least semi-quantitative. Thus, by measuring the response after a predetermined time, the analyst can obtain not only a positive indication of the presence of a particular constituent in a test sample, but also an estimate of how much of the constituent is present. Such strips provide the physician with a facile diagnostic tool as well as the ability to guage the extent of disease or bodily malfunction.

Illustrative of such strips currently in use are products available from the Ames Division of Miles Laboratories, Inc. under the trademarks CLINISTIX®, MULTISTIX®, KETOSTIX®, N-MULTISTIX®, DIASTIX®, DEXTROSTIX®, and others. Test devices such as these usually comprise one or more carrier matrices, such as absorbent paper, having incorporated with them a particular reagent or reactant system which manifests a color change in the presence of a specific test sample component. Depending on the reactant system incorporated with a particular matrix, these devices can detect the presence of glucose, ketone bodies, bilirubin, urobilinogen, occult blood, nitrite, and other substances. The specific color change and the intensity of the color observed within a specific time range after contacting the strip with the sample is indicative of the presence of a particular component and its concentration in the sample. Some of these test devices and their reactant systems are set forth in U.S. Pat. Nos. 3,123,443 (CLINISTIX®); 3,212,855 (KETOSTIX®); 3,814,668, 3,164,534 and 2,981,606 (DIASTIX®); and 3,298,789, 3,092,465, 3,164,534 and 2,981,606 (DEXTROSTIX®).

It is to those of the above-described devices having more than one reagent-bearing carrier matrix that the present invention is primarily applicable. Thus, a reagent strip can contain tests for more than one constituent in a particular liquid sample. For example, a single reagent strip could consist of a reagent-bearing carrier matrix responsive to glucose in urine, and another matrix spaced from but adjacent the first responsive to ketones, such as acetoacetate. Such a product is marketed by Ames Division under the name KETO-DIASTIX®. Another reagent strip marketed by Ames Division, N-MULTISTIX®, contains eight adjacent reagent-incorporated matrices and provides analytical measurements of pH, protein, glucose, ketones, bilirubin, occult blood, nitrite and urobilinogen.

Despite the obvious, time-proved advantages of such multiple test reagent strips as these, misuse can result in misinformation. These multiple-analysis tools comprise complex chemical and catalytic systems, each reagent matrix containing a unique reactive system, responsive to its particular analysate. Thus it is possible, if the reagent strip is misused, for chemicals to be transported by the liquid sample being analyzed from one carrier matrix on the strip to another. Should this happen it is possible for reagents from one carrier matrix to interfere with those of the others so contacted, causing unreliable results. Although it is common in the reagent strip industry to provide detailed instructions as to how this problem is avoided, i.e., directions for properly manipulating the reagent strips, nevertheless ignorance or disregard of these instructions could permit reagents from one matrix to run over onto an adjacent one. It is to the prevention of this "runover" problem that the present invention is primarily directed.

The elimination of runover has been long sought after, but until the advent of the present invention, never adequately attained. Applicants' discovery, which was the culmination of an extensive research effort based on their initial conception of how to avoid runover interference, has finally solved this elusive problem, and the results are indeed as unique as the solution.

2. Discussion of the Prior Art

The patent literature is replete with accounts of myriad attempts at curtailing runover, the great bulk of the emphasis being directed to two basic concepts: the absorbence of runover liquid by bibulous layers placed beneath the reagent-bearing layers of reagent strips; and use of hydrophobic barriers between the spaced matrices to confine the sample liquid to the matrices. The former has met with moderate success, whereas the latter has not. But more importantly, neither has completely obviated the problem.

Of the multi-layer type of reagent strips, only one is described in the literature as successfully curtailing the problem of runover, and its teachings are hereby incorporated in the present disclosure by reference. Thus, U.S. application Ser. No. 872,560, filed Jan. 26, 1978, issued as U.S. Pat. No. 4,160,008 on July 3, 1979 assigned to Miles Laboratories, Inc., describes a test device in which the carrier matrices containing reagent formulations are provided with absorbent underlayers which are separated therefrom by sample-impervious barrier layers. Each matrix thus forms the upper layer of a laminate composite in which the barrier layer is disposed between the matrix and the absorbent base layer, the composite being fixed to a suitable support such as a plastic strip. When the test device is dipped into a liquid sample, the portion of the sample which would otherwise runover from one matrix to another is largely absorbed into the underlayer of the latter through the exposed sides, the barrier layer of the composite segregating the absorbed runover from the upper reagent layer.

No other art appears to be directed to the absorptive underlayer approach to solving the runover problem, although other multilayered reagent strip devices are described in which potentially incompatible reagents for the same test are separated from each other in layers and communicate upon wetting by the test sample. For example, U.S. Pat. No. 3,531,254 teaches that potentially incompatible reagents can be impregnated into separate layers to permit extended storage periods before use. When such a multi-layered matrix is wetted with a test sample, these layers communicate and the reagents previously separated become mixed to give the desired analytical test.

Another example of a multi-layered carrier matrix is the one shown in U.S. Pat. No. 3,802,842. Here, a porous pad containing no reagents abuts an upper pad containing the reagents for the desired test. Thus, when liquid sample is applied to such a carrier matrix some of the sample is absorbed by the non-impregnated pad, and some by the one bearing the reagents. As in the previous patent, the layers of this carrier matrix communicate with one another when wet. Some of the liquid (and some of the reagents) pass through the upper pad into the lower pad. There is no barrier provided between the two pads.

There exist other patents which, although less pertinent than the previous two, nevertheless are of interest when considering the present invention, and are mentioned here for the convenience and information of those interested in the present teachings. U.S. Pat. No. 3,418,083 depicts an indicator-impregnated absorbent carrier matrix treated with wax, oil or similar "hydrophobic" agents. It is said that when a sample of blood is placed on such a reagent strip, only the colorless liquid components permeate it, the proteinaceous, colored blood components remaining on the surface where they can be removed. Thus, it is taught, the liquid portion bearing the analysate permeates the reagent pad, whereas color interferants are precluded from it.

Still another prior art reference, U.S. Pat. No. 3,672,845 assigned to the present assignee, shows spraying adhesive onto a plastic or paper support member for the purpose of gluing on reagent-laden polymer particles. Yet another, U.S. Pat. No. 3,992,158, teaches an upper, semipermeable layer containing ascorbate oxidase affixed to a lower, reagent-laden layer.

Turning now to the second of the abovementioned attempts to curb runover—hydrophobic barriers between adjacent test areas of a reagent strip - there has been a not inconsiderable amount of patenting activity. U.S. Pat. No. 3,001,915, assigned to the present assignee, describes an absorbent paper reagent strip having spaced reagent-impregnated test areas for more than one sample component, each such area being separated from its neighbor by a non-absorptive barrier portion. The barrier is provided by impregnation of the paper strip with such materials as polystyrene, rosin, paraffin and various cellulose esters. The reagent strip is prepared, according to this reference, by impregnating a portion of a paper strip with a glucose-sensitive reagent system. When dry, a solution of one of the above barrier materials is applied to the paper adjacent the glucose-sensitive portion. After further drying a protein-sensitive reagent system is applied. The process is repeated, with alternate applications of reagent and barrier solutions with drying steps in between.

Yet an earlier patent, U.S. Pat. No. 2,129,754 issued Sept. 13, 1938, describes the impregnation of filter paper with paraffin wax whereby specific areas are left unimpregnated, but surrounded by the wax. These unwaxed spots can then be treated with indicator systems for a particular analyte.

U.S. Pat. No. 3,006,735 carries the concept of barrier material impregnated between reagent areas of a paper strip one step further by providing successive reagent areas responsive to different degrees of water hardness. Between these reagent areas are impregnated such water repellent materials as oils, waxes, silicones and printers varnish. Like the preceding two patents, this reference is restricted to paper or like bibulous material wherein reagent and barrier material alike are impregnated sequentially along its length.

Similarly, U.S. Pat. Nos. 3,011,874 and 3,127,281 teach the use of hydrophobic barrier materials impregnated in part of a paper strip in order to separate one reagent area from another to avoid contamination.

A product was recently marketed by Eiken Chemical Co. Ltd., of Tokyo, Japan which was a 4-reagent area dip-and-read test strip responsive to pH, protein, occult blood and glucose in urine. The strip comprised a long plastic support member which was a composite of a lower polystyrene layer and an upper polyvinylchloride (PVC) layer. The reagents were impregnated in paper pads which were affixed to the PVC side of the composite support member. Contact angle measurements with this product revealed a contact angle of about 108° with distilled water. Since Applicants' first learning of this product, it appears that Eiken has withdrawn this configuration from the marketplace in deference to a new product whereby the PVC layer of the composite support member has been eliminated.

Finally, U.S. Pat. No. 3,964,871 mentions the separation of indicator reagent sites by non-absorbent or hydrophobic material.

Whereas the foregoing patents represent what is believed to be those most pertinent to the present invention, it should be noted that currently marketed reagent strip products for the most part comprise reagent-impregnated matrices affixed to a hydrophobic organoplastic strip. Thus, the multiple reagent strip known as N-MULTISTIX ®, marketed by the Ames Division of Miles Laboratories, contains eight different reagent-impregnated matrices mounted on a strip of polystyrene film. Since polystyrene is hydrophobic, the reagent strip can be said to have hydrophobic interstices between adjacent matrices.

Despite the lip service given by prior art accounts of eliminating runover, the fact remains that there are presently no reagent strips commercially available capable of stifling this problem to anywhere near the extent achieved by the present invention. Of the patent art cited above, only that approach disclosed in U.S.

Pat. No. 4,160,008, i.e., the use of an isolated absorbent underlayer, provides a real advance in the art. But even that approach, certainly widely divorced from the present invention, cannot approach the success at eliminating runover which the present invention achieves.

Prior art attempts using waxes, oils, silicones, etc. have not curtailed runover to a clinically significant extent; and what modest advances that may have been made were more than offset by serious drawbacks inherent to these attempts. For example, applying hydrophobic materials only at reagent area interstices embodies enormous technical problems, especially when compared with current techniques for manufacturing dip-and-read reagent strips. Besides the obvious extra steps required by intersticial application, there is the danger of some of the hydrophobic material overlapping the reagent areas—thus interfering with the paramount purpose of the device. Moreover, none of these prior art substances provides a suitable surface for adhesion. Small wonder no runover-free commercial products are available.

But even if these shortcomings were not prohibitive enough, the prior art hydrophobic substances lack the degree of hydrophobicity required to prevent runover. They do not provide a sufficient enough contact angle to achieve the required hydrophobicity, nor do they provide a suitable surface for binding either the absorbent matrices or the reagents themselves, were they to be coated directly on the hydrophobic surface. Only the present invention constitutes this long sought after breakthrough.

The present invention virtually eliminates cross-contamination between adjacent reagent areas of multiple test reagent strips. These results are truly incontrovertible. Nothing in the prior art approaches the dramatically high degree of success in solving this problem afforded by the presently disclosed concepts.

But the contribution of this discovery to the state of the art goes beyond the elimination of runover. Surprisingly, it has been found that adhesive techniques currently used for attaching reagent matrices to a polystyrene base support provide even stronger adhesive bonds when the present invention is utilized. Moreover, it is not necessary to utilize expensive process steps such as depositing hydrophobic coats between adjacent matrices. These and other advances in the current state of the art will become evident in view of the present specification and claims.

SUMMARY OF THE INVENTION

Briefly stated, the present invention relates to a test device for detecting the presence of a constituent in a liquid test sample and method for making it. It comprises a base support, a hydrophobic layer affixed to the base support and a test reagent affixed to a predetermined surface portion of the hydrophobic layer. The hydrophobic layer comprises a binder material, and finely divided silica particles having randomly covalently bound to their surfaces groups having the structure

wherein the R substituents, which can be the same or different, are hydrogen, lower alkyl or aryl.

BRIEF DESCRIPTION OF THE DRAWINGS

FIG. 1 is a side view of a preferred embodiment of the test device.

FIG. 2 depicts the contact angle subtended by a drop of distilled water on uncoated polystyrene film, whereas FIG. 3 shows a drop of distilled water on the same film when coated in accordance with the present teachings.

FIG. 4 is a graphic presentation of data obtained from comparing the invention with the prior art.

FIGS. 5 and 6 graphically present performance data from assays of occult blood and urobilinogen, respectively, in urine using the presently disclosed device.

FIGS. 7 and 8 present data from adhesive studies, and portray the performance of various adhesives on polystyrene film with and without application of the present inventive concepts.

Finally, FIG. 9 depicts the apparatus and method use in testing the adhesive propensity of polystyrene film coated with the presently described hydrophobic layer.

DETAILED DESCRIPTION OF THE INVENTION

Figure 1:
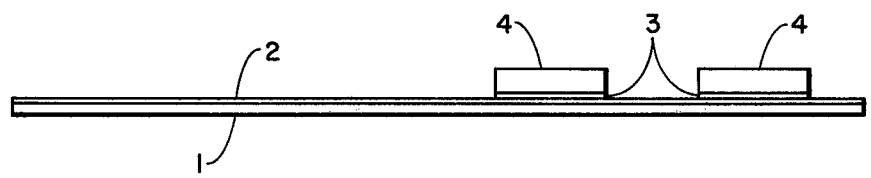
FIGS. 1-9 are provided to assist in illustrating and describing the presently-disclosed inventive concepts.

The test device of the present invention lends itself to the analysis of a liquid test sample for numerous constituents. In the case where the sample is beer, it can be used to determine the sugar content; hence, the extent of fermentation. It can be used to determine pH in such applications as battery acid strength determination. One area of exceptional importance is urinalysis, wherein the device can be used to determine such diverse urine constituents or characteristics as albumin, ascorbic acid, bilirubin, glucose, hydrogen ion, ketone, nitrite, occult blood, specific gravity and urobilinogen. Obviously the utility of this invention embraces the analysis of many more test sample constituents than those enumerated herein; thus the term "constituent" relates to any solution parameter, such as a solute or colligative property, for which a responsive reagent system can be devised. Equally diverse are the types of test samples which can be analyzed, including beer, industrial waste, urine, blood, and swimming pool water.

The reagents of the device constitute the heart of the analytical response provided by the device, and, in the broadest sense, include one or more reagent compositions respectively responsive to particular constituents—responsive in the sense that some detectable manifestation of the presence of the constituent takes place. The response can be in the form of the appearance of color, or its disappearance. One color may change to another. A change in the amount of light reflected or absorbed can be utilized. The analytical arts are replete with all of these types of detectable response, as well as others.

Thus, for example, if a response to glucose in urine is sought, the reagent composition could comprise the enzymes glucose oxidase and peroxidase and the indicator 3,3',5,5'-tetramethylbenzidine (TMB). In the presence of glucose this composition becomes colored various shades of blue, depending on the glucose concentration; ergo the detectable response is the appearance of blue. If the constituent is ascorbic acid, the composition might comprise methylene green and a suitable buffer. Ascorbate ion causes such a composition to fade from a dark blue to varying lighter shades of blue depending on the ascorbate concentration of the sample.

The base support member provides the main structural integrity of the test device, and it should therefore comprise a rigid or semi-rigid material. Ideally it comprises a dimensionally stable film of material such as polystyrene, polyolefin, polycarbonate, melamine resin or other polymer. Especially suitable is a biaxially oriented polystyrene film such as that manufactured by Plastic Suppliers, Inc. of Columbus, Ohio. The preferred shape is rectangular, being substantially long and narrow. Reagents, whether incorporated into matrices or otherwise, are affixed to areas which are generally closer to one end than the other, thus providing a reagent-free handle portion.

A truly unique feature of the present invention, and that aspect which gives rise to the advantages of elimination of cross-contamination between adjacent reagents and enhanced bonding with adhesives, is the hydrophobic layer applied to the base support. The layer comprises a hydrophobic material having a high contact angle and, if necessary, a suitable binding material such as a polymer soluble in an organic solvent, for example an acrylic polymer.

The hydrophobic material utilized in the present invention can vary in many respects, but it has been found particularly suitable to employ an alkylated fused silica, such as that known as Tullanox 500 available from Tulco, Inc. of North Billerica, Mass. Tullanox 500 is described by its manufacturer as an inorganic powdered silica (particle size about 0.007 micron) of low bulk density (about three pounds per cubic foot). It has an extremely high surface area which has been modified by reaction with an organic "silicone-like" compound (although not a silicone). Surface area has been calculated theoretically to be 325 meters$^2$/gram (m$^2$/g), and determined experimentally by the $N_2$ adsorption method to be 225 m$^2$/g. It is derived from a fumed silica base which is over 99.8 percent pure $SiO_2$. The hydrophilic hydroxyl groups inherent to the surface of such silica particles have been substituted with trimethyl siloxyl groups. The predominant physical attributes of this material are extremely fine particle size, very high surface area and almost complete lack of cohesive attraction between particles.

Although Tullanox 500 is the preferred material for the hydrophobic layer, it is to be understood that the present discovery is of such a pioneer nature as to extend much further in scope than merely Tullanox 500. For example, the siloxyl groups covalently bound to the silica can satisfy the general structure —O—SiR$_3$. The R substituents, which are all methyl in Tullanox 500, can also be hydrogen, lower alkyl, aryl, or any other group which provides the above-described advantages. By lower alkyl is meant substituted or unsubstituted alkyl groups having 1 to about 6 carbon atoms. Thus R can comprise methyl, ethyl, n-propyl, isopropyl, n-butyl, isobutyl, t-butyl, cyclobutyl and the various pentyl and hexyl isomers. The term aryl is intended to include aromatic groups, substituted or unsubstituted, phenyl or polynuclear, homocyclic or heterocyclic. Thus, R can comprise phenyl, tolyl, and nitrophenyl.

The hydrophobic layer also comprises a suitable binder to secure the hydrophobic material to the base support member, and it can take on many forms. For exmple, the silica material can be suspended in a solvent capable of partially dissolving the base support. In the case where the support member is polystyrene and the solvent contains benzene, partial dissolution of the polystyrene upon application of the suspension leads to binding of the silica to the support by the dissolved polymer after the residual solvent has evaporated. In this case the binder is the support member material itself.

Other manifestations of suitable binders are normally used coating materials such as polysiloxanes, polyacrylic resins such as poly(methylacrylic acid), poly(methylmethacrylate), acrylic copolymers, and others, as well as copolymers of vinyl chloride and other ethylenically unsaturated monomers.

Especially suitable for use as a binder is the acrylic copolymer utilized by Tulco, Inc. in the product known as Tullanox LC 410. This product comprises the finely divided Tullanox 500 particles, described supra, suspended in a solution of an acrylic copolymer in a liquid hydrocarbon. The physical properties of Tullanox LC 410, as provided by Tulco, Inc., are as follows:

| | |
|---|---|
| weight per gallon | 7.05 lb. |
| percent total solids | 16.00 grams/100 milliliters (g/ml) |
| percent solvents (Rule 66/3) | 84.00% |
| ratio of silica to polymer binder (wt./wt.) | 1.0 to 0.6 |
| clarity | opaque white |
| drying time (a) tack free | 60 minutes |
| (b) completely dry | 8 hours |

This suspension is infinitely dilutable in solvents, or combinations of solvents, having a K.B. value of 35 or higher. K.B. value is a measure of the aromatic content, hence the solvent power, of a hydrocarbon liquid. Kauri gum is readily soluble in butanol, but insoluble in hydrocarbons. Thus, the K.B. value is the measure of that volume of solvent required to produce turbidity in a standard solution containing kauri gum dissolved in butanol. Naphtha fractions have a K.B. value of about 30, whereas toluene is about 105.

It has been found to be desirable to dilute Tullanox LC 410 using various solvents. Especially beneficial is to utilize a solvent which partially dissolves or etches the base support member material. In the case where the support member comprises polystyrene, an aromatic solvent such as benzene or toluene facilitates an excellent hydrophobic finish which simultaneously offers excellent binding of the hydrophobic layer to the base support material.

The aforementioned reagent (or reagents) of the presently described test device is affixed by suitable means to the hydrophobic layer. The mode by which the reagent is affixed can take on a myriad of forms ranging from absorbent paper pads impregnated with the desired reagents to directly coated or imprinted reagents. In the former case the impregnated pad has traditionally been affixed utilizing a double-faced adhesive tape known as Double Stick sold by 3M Company.

Figure 7:
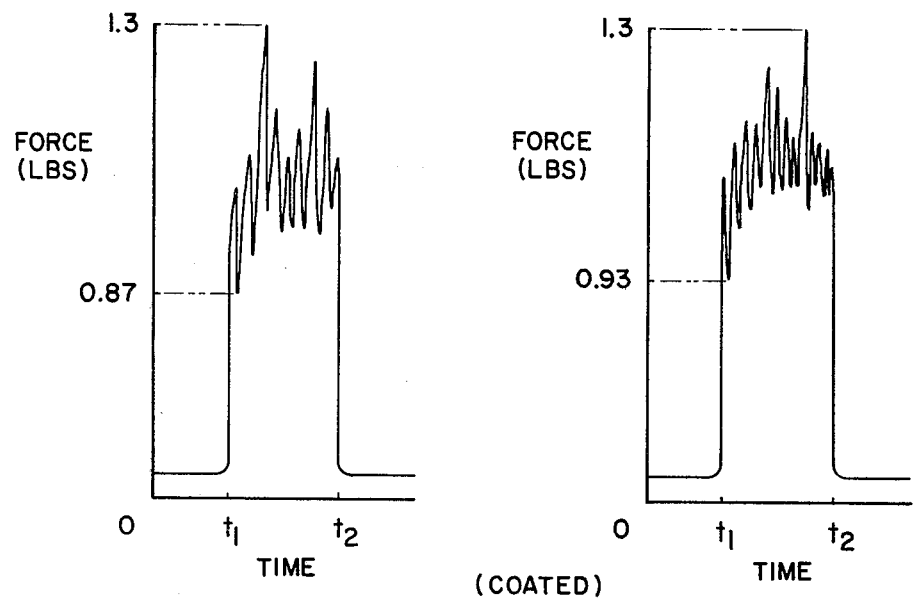
Figure 8:
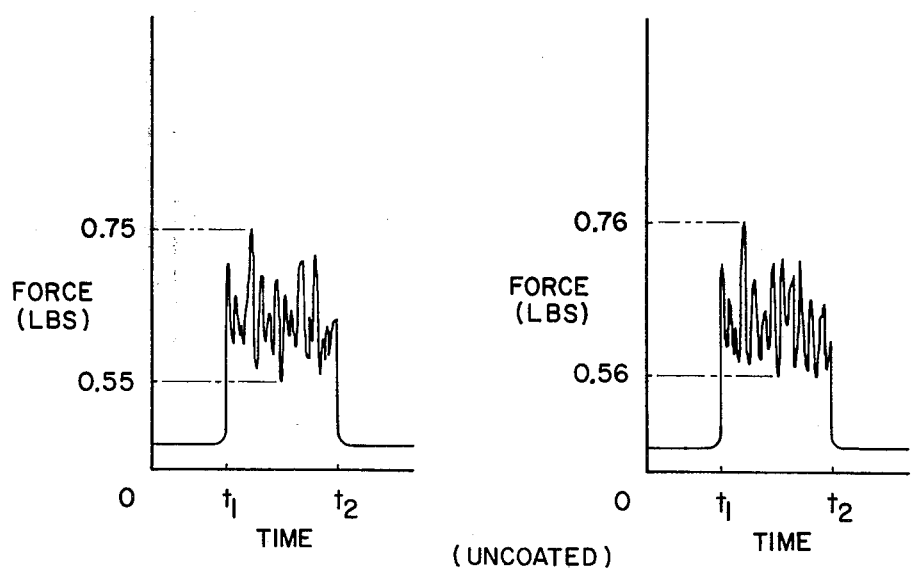

One of the surprising features of the present discovery is the increased affinity of this adhesive means for the hydrophobic layer as compared to the affinity of this same adhesive means for the preferred base support material, polystyrene, without the hydrophobic layer. FIGS. 7 and 8 portray this increased affinity graphically, FIG. 7 shows the amount of force required to remove two samples of Double Stick tape from polystyrene strips coated with Tullanox LC 410. The data for two of the samples are shown, and as can be seen, almost identical results were obtained, in excess of 0.8 pounds of force being required in each case. As shown in FIG. 8, removal of two samples of Double Stick tape from uncoated polystyrene required only about 0.5 pounds of force. The coating of the present invention dramatically enhanced the adhesive attraction of Double Stick adhesive for the support member. The experiments depicted by FIGS. 7 and 8 will be discussed further in the Examples, infra.

A preferred embodiment of the present invention, wherein many of the features discussed above are incorporated, is shown in FIG. 1. Thus, base support member 1 comprising biaxially oriented polystyrene film is coated with a thin film of Tullanox LC 410, which dries to form hydrophobic layer 2. The coating is achieved using a doctor blade or other suitable means known in the coating or printing art. A presently preferred method for applying the hydrophobic layer to the support member comprises the use of rotogravure printing techniques, techniques which are thoroughly known in the printing art. Specifically, the hydrophobic solution of Tullanox LC 410 is pumped into the fountain of a rotogravure press from which it is transferred to the printing cylinder. A film of polystyrene support material is passed through the press and the Tullanox solution is transferred to the film.

When the coating has been sufficiently dried, such as under ambient conditions or in an air oven at elevated temperature, the desired reagent-impregnated matrices 4 can be affixed to the layer 2 in spaced relation using a suitable adhesive as at 3. As is stated supra, the preferred adhesive is Double Stick tape. The preferred reagent matrices 4 comprise rectangular pieces of filter paper which are impregnated with solutions of reagent systems respectively responsive to particular analytes, dried, and mounted to the hydrophobic layer 2.

Figure 2:
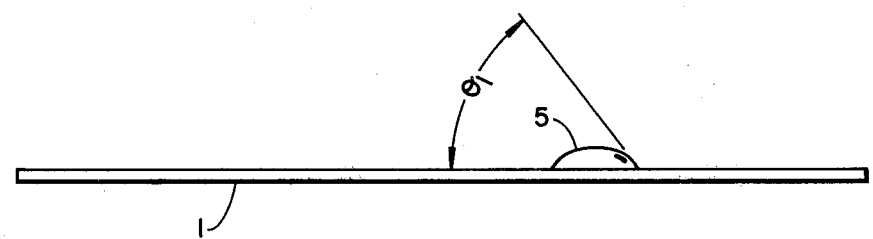
Figure 3:
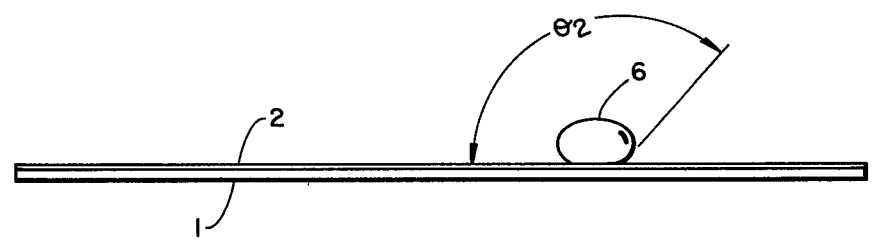

Although not the only criterion for successful elimination of runover, the concept of contact angle nevertheless plays a role of great significance. By definition, the term "contact angle", as it relates to a solid-liquid interface, means the angle subtended by the solid surface and a plane tangent to the surface of a liquid drop at the point of contact between the solid and the liquid. FIGS. 2 and 3 depict distilled water drops 5 and 6, respectively, resting on horizontal surfaces, and the contact angles are designated $\phi_1$, and $\phi_2$, respectively. The greater the contact angle caused by the particular solid surface; the greater the hydrophobicity of that surface. Likewise, the greater the hydrophobicity of the surface separating two reagent matrices of a test device such as in FIG. 1; the less likely is the occurrence of runover between such matrices.

FIG. 3 portrays a sheet 1 of biaxially oriented polystyrene film (Plastic Suppliers, Inc.) which has been coated with Tullanox LC 410 and dried to provide a hydrophobic layer in accordance with the present invention. The contact angle ($\phi_2$) between that surface 2 and a drop of distilled water 6 is about 135°. By comparison, uncoated polystyrene 1 in FIG. 2 effects a contact angle ($\phi_1$) of only about 50°.

EXAMPLES

The following Examples are provided to further illuminate the inventive aspects of the present discovery, and to further exemplify preferred embodiments. As such, they are intended as being merely illustrative, and are not to be construed as limiting the scope of the claims appended hereto.

Example I—Preparation of a Polystyrene Support Member

An experiment was conducted to prepare a polystyrene support member having an exceedingly high degree of hydrophobicity. Accordingly, sheets of biaxially oriented polystyrene obtained from Plastic Suppliers, Inc. were coated with varying dilutions of Tullanox LC 410. The Tullanox formulation was diluted with varying amounts of a solvent mixture comprising 65° petroleum ether, acetone, and toluene. The Tullanox LC 410, which contains 16% by weight total solids, was diluted with enough solvent mixture to make four suspensions containing 3.2, 2.4, 1.6 and 0.8 grams of Tullanox 500 particles per 100 grams of suspension. Four sets of coated polystyrene were prepared, using a 10 mil doctor blade, and these were designated A, B, C and D, respectively. The following table synopsizes these formulations. The films cast in this manner were subsequently dried for three minutes using a laboratory fan operated heat gun.

| Component | A | B | C | D |
|---|---|---|---|---|
| Tullanox LC 410 | 1.0 g | 0.75 g | 0.50 g | 0.25 g |
| Petroleum Ether | 3.4 ml | 3.65 ml | 3.90 ml | 4.15 ml |
| Toluene | 0.3 ml | 0.3 ml | 0.3 ml | 0.3 ml |
| Acetone | 0.3 ml | 0.3 ml | 0.3 ml | 0.3 ml |
| Tullanox 500 (grams per 100 grams of solution applied) | 3.2 | 2.4 | 1.6 | 0.8 |

After drying, the coated sheets were held at an angle of 45° and ten microliter drops of water were placed on each treated sheet. All of sheets A, B, and C shed all of the water placed upon them. Sheet D, the one with the 0.8% solids, did not shed all its water but was observed to be extremely hydrophobic nonetheless.

Example II—Contact Angle Determinations

In order to examine the relative hydrophobicity of uncoated polystyrene film compared with coated version B of Example I, an experiment was performed to measure the contact angles produced by each. Photographs were taken of drops of distilled water on horizontally oriented polystyrene sheets, one coated as in Example IB, the other uncoated. The photographs were taken along the plane of the film, i.e. side views, and the resultant images were developed as negative, and mounted on slides suitable for screen projection. Screen projection enabled considerable magnification, thus simplifying contact angle measurements, as well as permitting great accuracy of measurement. FIGS. 2 and 3 simulate the resultant photographs, FIG. 2 representing the uncoated polystyrene sheet, and FIG. 3 the coated sheet B of Example I.

The measurements were performed in triplicate for each sheet, and the results are set forth in the following table.

| Polystyrene Sheet | Contact Angle | | |
|---|---|---|---|
| Example I, B | 133° | 135° | 134° |
| Uncoated | 53° | 49° | 53° |

Example III—Preparation of Test Devices

A laboratory experiment was performed wherein a test device was prepared having multiple reagent-impregnated matrices, each responsive to a different urine constituent. The object of this experiment was to demonstrate the concepts of the present invention, whereby the occurrence of runover from one matrix to another following immersion in and removal from a test sample such as urine is dramatically curtailed. The reagent matrices of this device approximate those of the commercially available product known as N-MULTISTIX. The urine parameters corresponding to the reagent matrices are pH, albumin, bilirubin, urobilinogen, nitrite, occult blood, glucose and ketone.

A sheet of biaxially oriented polystyrene film manufactured by Monsanto Company (essentially the same as the Plastic Suppliers, Inc. material described supra) was coated with a solution of Tullanox LC 410. A casting block capable of leaving a wet film of 5 mil thickness was used for this purpose. The Tullanox formulation obtained from the manufacturer, Tulco, Inc., was diluted with varying amounts of a solvent comprising 65° petroleum ether, acetone, and toluene as in Example I. The Tullanox LC 410 contains 16% by weight total solids, and was diluted with enough solvent mixture to make three suspensions containing 1.6, 2.4 and 3.2 grams of Tullanox 500 particles per 100 grams of suspension (g%). This resulted in three sheets of plastic, each containing a different amount of Tullanox methylated silica.

After drying, the reagents were applied to the coated polystyrene using ribbons of filter paper which had been impregnated with appropriate reagents for the particular urine constituent to be measured. To accomplish this, a layer of Double Stick adhesive tape was applied to one side of each of the impregnated ribbons, and the exposed adhesive side of the ribbon/tape composite was then applied to the hydrophobic coated polystyrene, along the lengthwise dimension, in spaced parallel stripes. Eight paper ribbons, responsive to each of pH, protein, glucose, ketone, bilirubin, occult blood, nitrite, and urobilinogen, respectively, were applied to the coated polystyrene in reverse order beginning from the edge of the polystyrene sheet. The reagent formulations were all based on standard chemistries available in the art.

After applying the reagent-impregnated ribbons to the polystyrene support member, the laminate was then sliced along the width dimension to produce test strips measuring 4 inches by 0.2 inches. These crude, laboratory-made test devices were then used to evaluate the reduction in runover attributable to the hydrophobic coating.

Example IV—Comparison of the Test Device with Other Devices Capable of Measuring the Same Urine Parameters The devices of Example III were used for comparison with similar devices prepared in similar fashion, and with devices presently commercially available.

One set of reagent strips was prepared for use in this comparison exactly as those of Example III except the hydrophobic coating was omitted. The strips were identical to those of Example III in every other aspect.

Another set of reagent strips was prepared in the same fashion except that, in addition to omitting the hydrophobic layer, absorbent underlayers were provided to certain reagent matrices. These were prepared in the manner set forth in U.S. patent application Ser. No. 872,560, mentioned supra, and made a part hereof. The reagent matrices provided with absorbent underlayers were pH, protein, bilirubin, occult blood and nitrite. These underlayers were separated from their respective reagent matrices by barrier layers of Double Stick tape. Accordingly, these strips were the same as in Example III, with two important exceptions: there was no hydrophobic layer affixed to the support member, and there were absorbent underlayers beneath five of the eight reagent matrices.

In addition, the devices of Example III were compared with commercially available products known as Chemstrip 8 (Boehringer Mannheim GmbH), and Rapignost Total Screen and Rapignost Organoprofil (Behringwerke AG).

The test devices were dipped in urine samples containing 100 milligrams/deciliter (mg%) protein, 250 mg% glucose, 0 mg% ascorbate, and having a specific gravity of 1.007 and a pH of 8.5.

The study to evaluate runover was performed by multiple personnel, each of whom performed an evaluation of each reagent area. The data was recorded and averaged, and standard deviations calculated.

The technique utilized in this study encouraged the occurrence of runover. The method was deliberately violative of instructions accompanying commerically available multiple reagent test devices. Thus, the study was conducted by dipping each reagent strip in urine and, upon removal, immediately inverting it to the handle down position, and holding it in that position while examining the reagent matrices. This technique is explicitly proscribed in the directions for use accompanying similar commerically available products, because of the probability of cross-contamination of reagents. The data obtained from this experiment thus reflects runover occurrence at its worst.

The readings recorded in the following table comprise observations of aberrant color formation in the various reagent matrices. In each case, the observer examined each reagent matrix and estimated the percentage of its surface which appeared to be aberrantly colored from the occurrence of runover. No data is reported for the urobilinogen matrices (with exceptions as indicated in the table), because when the strips were held in their inverted position (handle down) the urobilinogen matrix was uppermost, and therefore unaffected by runover.

The results of this experiment are tabulated below:

| | % OF REAGENT AREAS AFFECTED BY RUNOVER (REAGENT AREAS LISTED IN ORDER OF POSITION ON STRIP FROM HANDLE) | | | | | | | |
|---|---|---|---|---|---|---|---|---|
| Strip | No. of Readers | pH | protein | glucose | ketone | bilirubin | occult blood | nitrite |
| Example III with no hydrophobic coating | 21 | 64.5 | 19.3 | 6.0 | 14.5 | 31.9 | 21.7 | 10.2 |
| Example III with no hydrophobic coating and with | | | | | | | | |

-continued

| % OF REAGENT AREAS AFFECTED BY RUNOVER (REAGENT AREAS LISTED IN ORDER OF POSITION ON STRIP FROM HANDLE) | | | | | | | | |
|---|---|---|---|---|---|---|---|---|
| five underpads* | 21 | 23.1* | 0.71* | 2.5 | 9.8 | 10.0* | 9.0* | 4.9* |
| Example III (1.6% Tullanox) | 10 | 11.7 | 0 | 3.5 | 1.0 | 6.5 | 0 | 9.5 |
| Example III (2.4% Tullanox) | 10 | 3.8 | 0 | 9.0 | 0 | 6.5 | 0 | 7.2 |
| Example III (3.2% Tullanox) | 10 | 0 | 0 | 5.0 | 0 | 1.5 | 0 | 7.0 |
| | | nitrite | pH | protein | glucose | ketone | urobilinogen | bilirubin |
| Chemstrip 8 | 22 | 3.2 | 64.7 | 12.7 | 21.1 | 2.5 | 1.8 | 16.1 |
| | | nitrite | pH | occult blood | protein | glucose | ketone | bilirubin |
| Rapignost Total Screen | 10 | 5.5 | 44.5 | 10.5 | 23.5 | 38.0 | 2.5 | 0 |
| | | nitrite | pH | occult blood | protein | bilirubin | | |
| Rapignost Organoprofil | 10 | 3.2 | 46.8 | 10.9 | 11.8 | 0 | | |

It should be borne in mind by the reader, while examining the data in the above Table, that the positioning of reagent matrices for Chemstrip 8 and the two Rapignost devices is different from that of Example III and the variations thereof prepared for the present example. Accordingly, because of the difference of positioning of the respective reagent matrices on the commercial strips, the manifestations of runover are different from those of the remaining strips. This is because different reagents are dissolved by the sample drops and transported to neighboring matrices. Accordingly, although the data presented in the Table and plotted in FIG. 4 are extremely useful in assessing the efficacy of the present invention, nevertheless the absoluteness of the data is somewhat detracted from by the above considerations.

Figure 4:
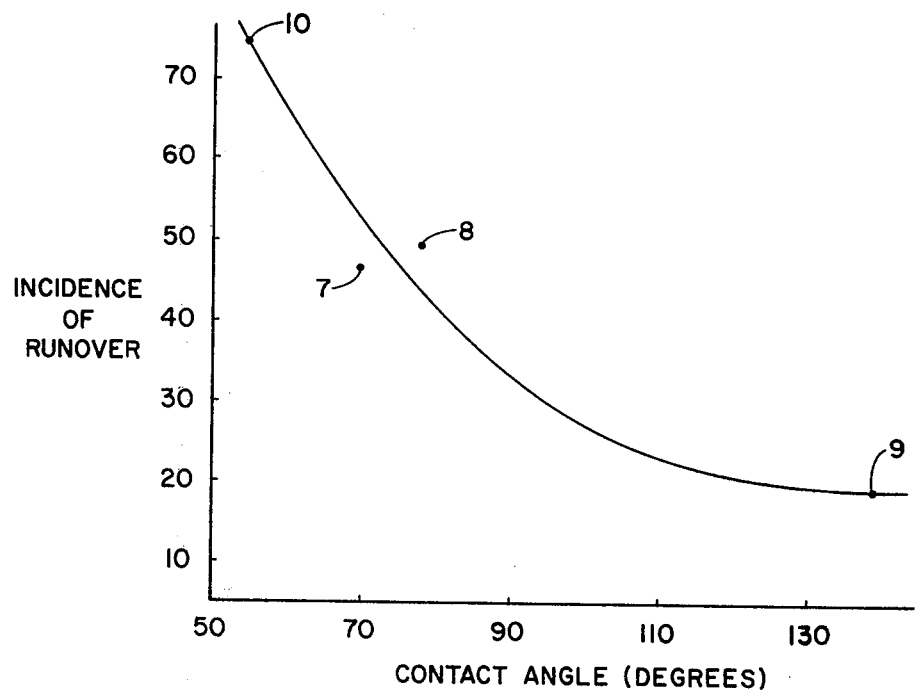

The average readings for some of the reagent strips tested were themselves averaged and plotted versus contact angle of the base support member between reagent areas in FIG. 4. The data for strips prepared as in Example III without hydrophobic coating or underpads correspond to point 10, Chemstrip 8 to point 8, Rapignost Total Screen to point 7 and a strip of the present invention (Example III, 2.4 g% solids) to point 9.

The graph shows a remarkable diminution in the incidence of runover directly attributable to the presently claimed concepts. Moreover, the data in the graph was obtained under the most adverse of conditions, adverse to the extent that laboratory-prepared uncoated strips showed an average runover incidence of almost 74%, whereas the same laboratory-prepared strips with the hydrophobic layer of the present invention reduced this figure to a mere 19%. Currently available commercial products tested showed an average runover incidence of about 47 to 50%.

Example V—Effect of Hydrophobic Coating on Reagent Area Performance

An experiment was performed to determine whether the use of the hydrophobic coating of the present invention has an adverse effect upon standard analytical reagents. Specifically, test strips were prepared in accordance with Example III having reagent matrices responsive to occult blood and urobilinogen. The hydrophobic coating corresponded to Tullanox LC 410 diluted to 2.4 g% Tullanox 500. Another set of strips was prepared in identical fashion except that no hydrophobic layer was applied to the polystyrene support member. Strips from each set were used to detect the levels of occult blood and urobilinogen in urine samples. The results given by the strips were then plotted versus the actual concentrations of these urine constituents.

Figure 5:
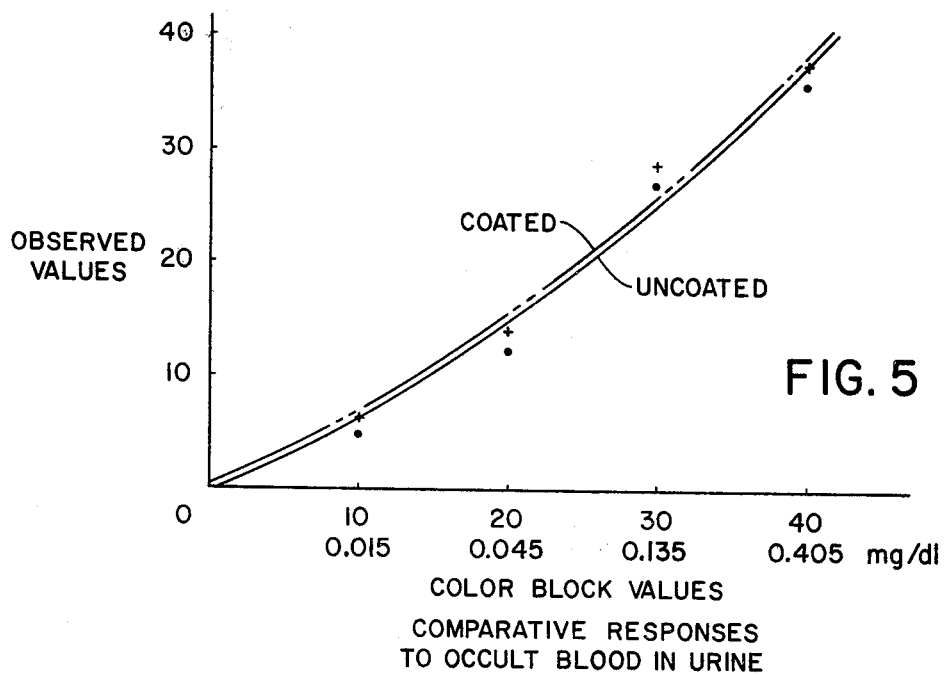
Figure 6:
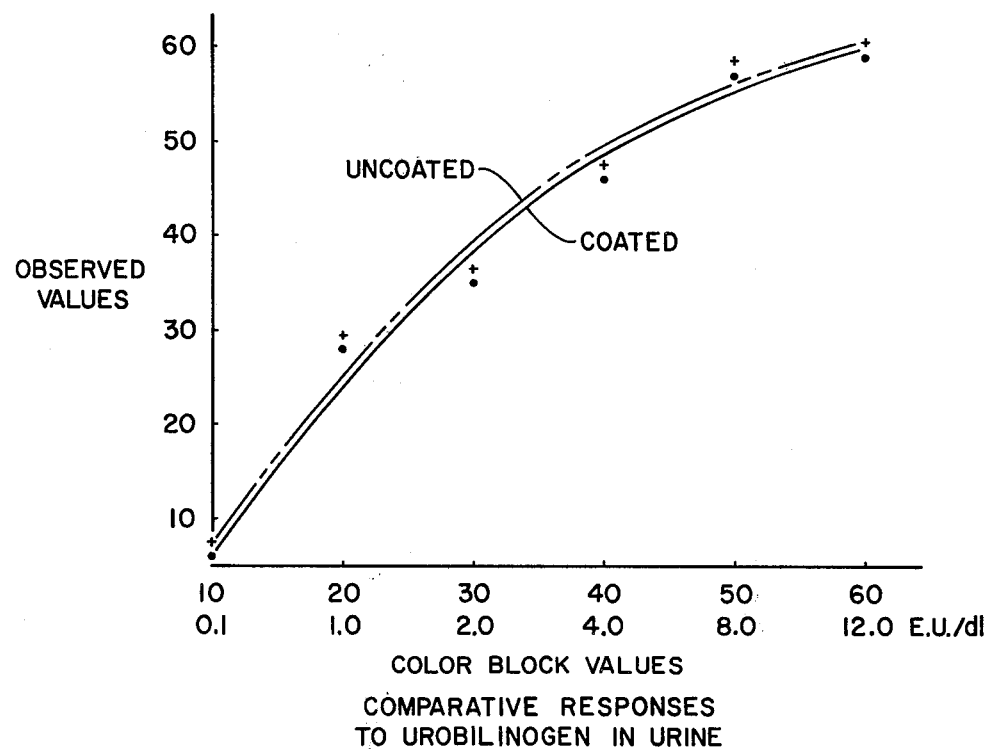

The data obtained from this experiment is plotted in FIGS. 5 and 6, the former showing occult blood data, the latter urobilinogen. As can be seen from these graphs, the strips of the present invention (designated "coated") demonstrated almost identical correlation of observed values to color block values as did identical strips with no hydrophobic layer (designated "uncoated"). Thus, the presently claimed concepts had no adverse effect on the performance of the occult blood and urobilinogen reagent systems studied.

Example VI—Effects of the Hydrophobic Layer on Adhesive Strength

Because of the desirability of applying the concepts of the present invention to current reagent strip technology, whereby reagent matrices are secured to support members using adhesive means such as Double Stick Type 415 tape, an experiment was conducted to explore the bonding strength between that adhesive means and the hydrophobic layer applied to polystyrene. Hence, polystyrene sheets were coated with Tullanox LC 410. The resultant dried films were compared with uncoated polystyrene by measuring their respective bonding strengths with Double Stick tape.

Figure 9:
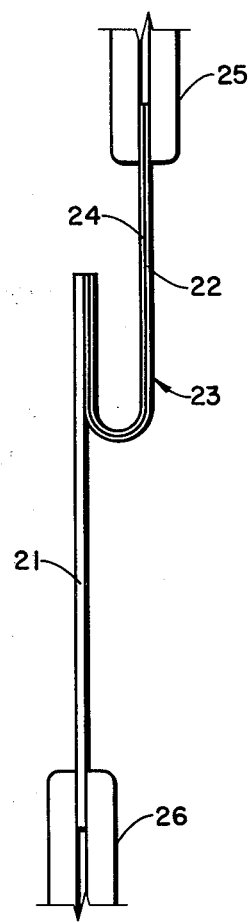

The coated polystyrene film was prepared in accordance with Example I, B. The same polystyrene used in Example I, without coating, was used for the comparison. Adhesive bonding strength, or adhesion, was measured using a tensile tester known as an Instron Table Model TM Universal Measuring Instrument, obtainable from the Instron Corporation, Canton, Massachusetts. This test is illustrated in FIG. 9, wherein the instrument has upper jaws 25 and lower jaws 26 to which opposite ends of a sample material can be attached. The instrument is capable of applying force to these jaws such that they move away from one another at a constant predetermined rate of speed. The amount of resistance caused by the sample between the jaws is measured on a graph whereby force is plotted versus unit time. FIGS. 7 and 8 are representations of the chart readings which were obtained in this experiment, and these will be further identified below.

The sample was prepared by applying one of the adhesive sides of Type 415 Double Stick double-faced adhesive tape to filter paper such as that used for reagent matrices on commercially available reagent strips (Eaton-Dikeman No. 204). The filter paper/adhesive composite was then cut into strips measuring 5 by 0.2 inches. Thus one side of the adhesive tape was bound to the paper, the other adhesive side still being covered by the easily removable protective paper. A two inch portion of the protective paper was removed, thus exposing two inches of adhesive on each five inch strip of paper/adhesive laminate. Two of these strips were then secured to a piece of polystyrene sheet, care being taken to apply only slight pressure in affixing the paper/adhesive strip to the plastic. A platen was then positioned over the prepared sample covering both of the strips and a ten pound weight placed on top of it for one minute. This latter procedure assures uniform application of the adhesive to both coated and uncoated polystyrene.

Immediately following the one minute weighting period, the polystyrene sheet was sliced between the adhesive strips, thereby yielding two samples of polystyrene each with its own paper/adhesive composite adhered to it. These samples were then tested with the Instron machine.

The samples were secured in the jaws of the machine as illustrated in FIG. 9. The unsecured end of the paper/adhesive composite 23, comprising paper layer 24 and Double Stick layer 22, was fastened in upper jaw 25. The tape was then bent as shown and the lower end of the polystyrene sheet 21 was secured in lower jaws 26 of the Instron instrument. In operation of the instrument, the jaws 25 and 26 were moved away from one another as described above.

FIG. 7 depicts the results obtained with polystyrene coated with Tullanox LC 410, whereas FIG. 8 shows the data yielded from the same experiment except that uncoated polystyrene was used. The data of FIGS. 7 and 8 clearly show the enhanced adhesion between Double Stick tape and a polystyrene sheet bearing the hydrophobic layer of the present invention. The force required to separate the paper/adhesive composite from the coated support member was about 0.8 pounds (FIG. 7) whereas the uncoated required only about 0.5 pounds (FIG. 8).

Prior art attempts at applying hydrophobic coatings such as wax, oil and silicones resulted in failure because the coating would not adhere sufficiently to adhesives for mounting carrier matrices. The foregoing Example demonstrates that this problem does not exist when the presently-described concepts are utilized. In fact, the adhesive propensity of polystyrene for Double Stick adhesive tape is actually dramatically increased.

While the examples illustrate the advantages of the invention with respect to those forms in which the reagents are affixed to the hydrophobic layer via incorporation in absorbent matrices, it is understood that the advantage of greatly reduced runover is also inherent in those forms of the invention wherein the reagents are affixed to the hydrophobic layer by other means, for example printing or coating directly onto said layer.

What is claimed is:

1. In a test device for analyzing a test sample for the presence of one or more constituents, the device comprising a base support member, a hydrophobic layer affixed to the support member, and two or more reagent compositions affixed to the hydrophobic layer, each respectively responsive to a particular sample constituent or concentration thereof, the improvement wherein said hydrophobic layer comprises finely divided silica particles having covalently affixed to the surfaces thereof groups having the structure —O—SiR₃ wherein said R substituents, same or different, are hydrogen, lower alkyl, or aryl; and a suitable binder.

2. The improvement of claim 1 wherin the R substituents are all lower alkyl.

3. The improvement of claim 1 wherein the R substituents are all methyl.

4. The improvement of any of claims 1-3 wherein each reagent is incorporated, respectively, with a hydrophilic carrier matrix, each matrix being affixed to the hydrophobic layer.

5. The improvement of any of claims 1-3 wherein each reagent, respectively, is incorporated with a paper carrier matrix, each matrix being affixed to the hydrophobic layer.

6. The improvement of any of claims 1-3 wherein the binder is an acrylic polymer.

7. The improvement of claim 1 wherein the base support member is a polystyrene film, the R substituents in the hydrophobic layer are lower alkyl, the binder is an acrylic polymer, and the reagent compositions are incorporated, respectively, with hydrophilic carrier matrices.

8. The improvement of claim 7 wherein the reagent compositions are responsive, respectively, to albumin, bilirubin, glucose, hydrogen ion, ketone, nitrite, occult blood, urobilinogen or combinations thereof.

9. The improvement of claim 8 wherein reagent compositions are additionally provided which ae responsive to ascorbic acid, specific gravity or both.

10. A method for preparing a test device capable of determining the presence of a constituent in a test sample wherein the device has the property of eliminating the occurrence of runover, the method comprising the steps of preparing a hydrophobic coating material comprising (a) finely divided silica particles having covalently affixed thereto groups having the structure -O-SiR₃, wherein the R substituents, same or different, are hydrogen, lower alkyl or aryl, and (b) a suitable binder, affixing the hydrophobic coating material to a base support member to form a hydrophobic layer on the support member, and affixing to the hydrophobic layer a reagent capable of producing a detectable response in the presence of the test sample constituent.

11. The method of claim 10 wherein said reagent is incorporated with a hydrophilic carrier matrix which is affixed to said hydrophobic layer.

12. The method of claim 10 wherein said reagent is incorporated with a paper carrier matrix which is affixed to said hydrophobic layer.

13. The method of claim 10 which includes the additional steps of affixing to the hydrophobic layer additional reagents respectively responsive to other constituents of a test sample, said reagents being affixed to the hydrophobic layer in spaced relation to each other.

* * * * *